(12) United States Patent
Loeffler et al.

(10) Patent No.: US 8,350,240 B2
(45) Date of Patent: Jan. 8, 2013

(54) DEVICE AND METHOD FOR GENERATING AND DETECTING COHERENT ELECTROMAGNETIC RADIATION IN THE THZ FREQUENCY RANGE

(75) Inventors: Torsten Loeffler, Glashütten (DE); Hartmut G. Roskos, Kronberg (DE); René Beigang, Trippstadt (DE)

(73) Assignee: Johann Wolfgang Goethe-Universitat, Frankfurt am Main (DE)

( * ) Notice: Subject to any disclaimer, the term of this patent is extended or adjusted under 35 U.S.C. 154(b) by 251 days.

(21) Appl. No.: 12/602,291

(22) PCT Filed: May 21, 2008

(86) PCT No.: PCT/EP2008/056279
§ 371 (c)(1),
(2), (4) Date: May 13, 2010

(87) PCT Pub. No.: WO2008/145588
PCT Pub. Date: Dec. 4, 2008

(65) Prior Publication Data
US 2010/0213375 A1    Aug. 26, 2010

(30) Foreign Application Priority Data
Jun. 1, 2007  (DE) .......................... 10 2007 025 891

(51) Int. Cl.
*G01J 3/10* (2006.01)
(52) U.S. Cl. ................. 250/504 R; 250/493.1
(58) Field of Classification Search ............. 250/338.1, 250/339.07, 340, 341.1
See application file for complete search history.

(56) References Cited

U.S. PATENT DOCUMENTS

| 5,789,750 A | 8/1998 | Nuss |
| 5,866,896 A | 2/1999 | Georgiades et al. |
| 6,388,799 B1* | 5/2002 | Arnone et al. ................ 359/326 |
| 6,697,186 B2 | 2/2004 | Kawase et al. |
| 6,903,341 B2* | 6/2005 | Imai et al. ..................... 250/340 |
| 2002/0024718 A1* | 2/2002 | Kawase et al. ................ 359/330 |
| 2004/0017833 A1* | 1/2004 | Cundiff et al. .................. 372/18 |

FOREIGN PATENT DOCUMENTS

| DE | 102004021869 A1 | 1/2005 |
| DE | 102004054408 A1 | 2/2007 |
| GB | 2347756 A | 9/2000 |
| WO | 90/04867 A1 | 5/1990 |

OTHER PUBLICATIONS

K. Kawase et al., "Terahertz wave parametric source", Journal of Physics D. Applied Physics, IOP, Publishing, Bristol, GB, Jan. 22, 2002, Seiten R1-R14, XP002348893.

(Continued)

*Primary Examiner* — Marcus Taningco
(74) *Attorney, Agent, or Firm* — Paul & Paul

(57) ABSTRACT

The present invention concerns a device for generating and detecting coherent electromagnetic radiation (8) in the THz frequency range, comprising an optically parametric oscillator (2) for generating electromagnetic radiation in the THz frequency range (8). To provide a device for generating and detecting electromagnetic radiation in the THz frequency range it is proposed in accordance with the invention that it has a coherent phase-sensitive detector (3, 21) for detecting intensity and phase of the electromagnetic radiation (8) generated by the optically parametric oscillator (2).

9 Claims, 3 Drawing Sheets

OTHER PUBLICATIONS

Figure 1:
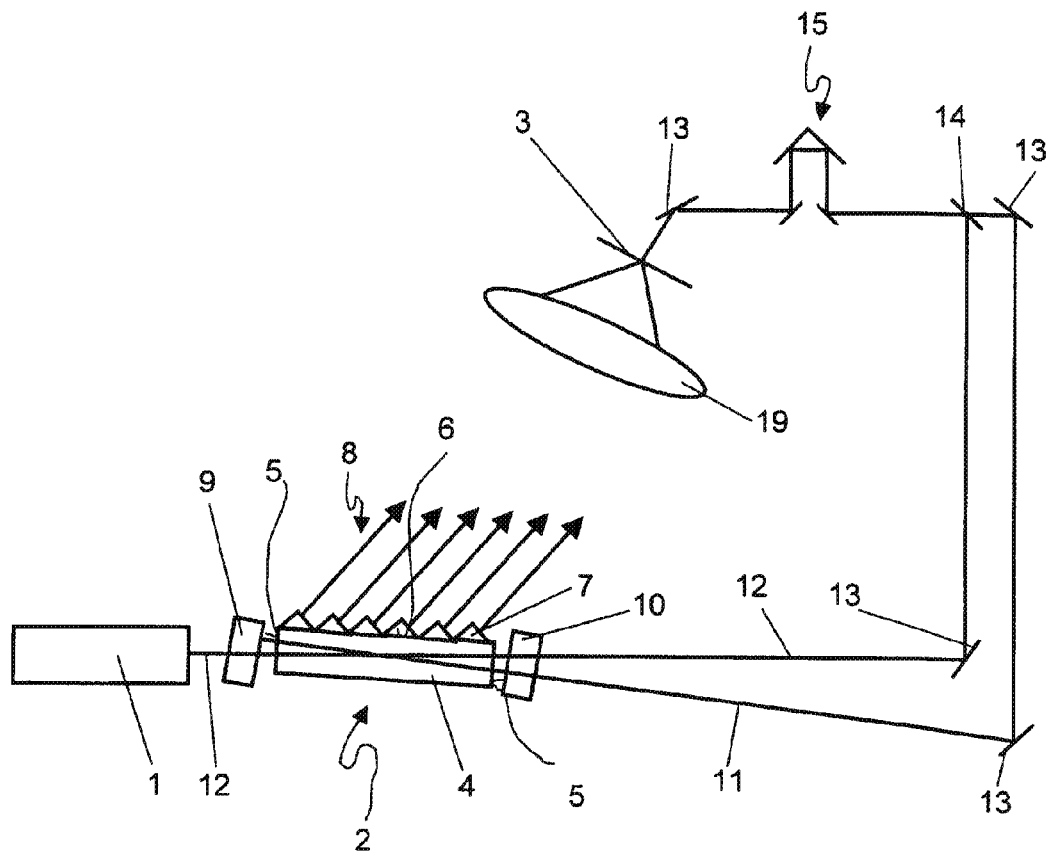

Guo R et al: "Detection of coherent tunable THz-wave using of stimulated polariton scattering in MgO: LiNbO3", Proceedings of SPIE—vol. 6582, Research Institute of Electrical Communication (RIEC), Tohoku University, XP-002496498.

Cao Hua et al: "Coherent detection of pulsed narrowband terahertz radiation" Applied Physics Letters, AIP, American Institute of Physics, Melville, NY, Bd. 88, Nr. 1,. Jan. 3, 2006, Seiten 11101-011101, XPO12080343, ISSN: 0003-6951.

Kawase K. et al: "Terahertz wave 1,10 parametric source", Journal of Physics D. Applied Physics, IOP Publishing, Bristol, GB, Bd. 35, Nr. 3. Feb. 7, 2002, Seiten.

Masatsugu Yamashita, "Component spatial pattern analysis of chemicals by use of two-dimensional electro-optic terahertz imaging", Applied Optics/vol. 44, No. 25/ Sep. 1, 2005, pp. 5198-5201.

* cited by examiner

DEVICE AND METHOD FOR GENERATING AND DETECTING COHERENT ELECTROMAGNETIC RADIATION IN THE THZ FREQUENCY RANGE

The present invention concerns a device for generating and detecting coherent electromagnetic radiation in the THz frequency range comprising an optically parametric oscillator for generating electromagnetic radiation in the THz frequency range.

The present invention also concerns a method of generating and detecting coherent electromagnetic radiation in the THz frequency range, wherein an optically parametric oscillator is used for generating electromagnetic radiation in the THz frequency range.

In the frequency range between 100 GHz and 10 THz, also referred to as the far infrared spectral range, many materials such as for example paper and a series of plastic materials are transparent and can be transilluminated. Water in contrast has strong absorption lines at those frequencies. In addition there are potential applications in particular for imaging THz systems, for example for examining biomedical tissue, wherein the differing water content between healthy and pathological tissue makes it possible for example to record a high-contrast image, quality control procedures, packaging controls, security controls and monitoring chemical reactions. In that respect the frequency of 1 THz corresponds to a wavelength of the electromagnetic wave of 300 µm and a photon energy of 4.14 eV or 33 wave numbers.

In comparison with X-radiation which is conventionally used for most of the aforementioned applications THz radiation has the advantage of low photon energy levels, that is to say it does not involve harmful effects which are dangerous to health due to ionising radiation.

Motivated by those potential applications, in past years different sources for generating coherent THz radiation have been developed. U.S. Pat. No. 6,697,186 B2 discloses a THz wave generator having a non-linearly optical crystal for parametric generation and a first laser device for injecting a monofrequency first laser beam as a pump wave in the non-linearly optical crystal. With that arrangement it is possible for a THz wave to be generated by use of the parametric effect in the non-linearly optical crystal under a non-colinear phase matching condition, whereby the power of the THz wave is increased and its spectral width is constricted.

The overview article by Kodo Kawase et al 'Terahertz parametric sources and imaging applications', *Semicond. Sci. Technol.* volume 20 (2005), pages 258 ff describes an optical parametric oscillator which for generating coherent tunable THz waves uses efficient parametric dispersion of laser light by way of a polariton (stimulated polariton dispersion) in a non-linearly optical crystal. A polariton is a quantum of a coupled transverse phonon-photon wave field and stimulated polariton dispersion occurs if the pump excitation of polar crystals is sufficiently strong. Such polar crystals are for example lithium niobate (LiNbO$_3$), lithium tantalate (LiTaO$_3$) and gallium phosphite (GaP) which are both infra-red-active and also Raman-active. The dispersion process includes both non-linear processes of the second and also the third order. Therefore a strong interaction occurs between the pump wave, an idler wave and the polariton or signal wave, the polariton wave being the THz wave to be generated.

The THz systems which are known from the state of the art and which use optically parametric oscillators for generating THz radiation detect or register the radiation generated in that way by means of conventional thermal detectors. Those thermal detectors are in particular pyroelectric detectors and bolometers. To permit an adequate signal-to-noise ratio, they have to be operated at low temperatures, that is to say in a cryogenic environment. That means that such detectors are complicated and expensive to construct and are only suitable for laboratory or research operation. In addition the conventional thermal detectors only permit detection of the power or intensity incident on the detector element, but not the phase of the THz radiation. It is precisely the phase information however that entails a considerable potential for obtaining information, in particular for spectroscopic and imaging applications.

In comparison with that state of the art therefore the object of the present invention is to provide a device for generating and detecting electromagnetic radiation in the THz frequency range, wherein an optically parametric oscillator is used for generating the THz radiation and the detector permits operation at ambient temperature under everyday conditions.

To contribute to attaining that object in accordance with the invention there is proposed a device for generating and detecting coherent electromagnetic radiation in the THz frequency range, comprising an optically parametric oscillator for generating electromagnetic radiation in the THz frequency range, wherein the device has a coherent phase-sensitive detector for detecting intensity and phase of the electromagnetic radiation generated by the optically parametric oscillator.

In that case an optically parametric oscillator in accordance with the present invention has a polar non-linearly optical crystal for example of lithium niobate (LiNbO$_3$), lithium tantalate (LiTaO$_3$) or gallium phosphite (GaP). In that respect the optically parametric oscillation for generation of the THz radiation is based on the phonon-like behaviour of polaritons in the region of the resonance frequency (near the TO-phonon frequency). However the polaritons behave like photons in the non-resonant low-frequency THz range where a signal photon at the THz frequency ($\omega_T$) and an idler photon ($\omega_i$) are generated parametrically from a provided pump photon ($\omega_p$) radiated into the crystal. In accordance with the law of the conservation of energy in that respect $\omega_p=\omega_T+\omega_i$. In that respect the indices p stand for pump, T for THz and i for idler. The law of pulse conservation also applies in the stimulated dispersion process, $\vec{k}_p=\vec{k}_i+\vec{k}_T$. That leads to an angle-dispersive behaviour in respect of the idler and THz waves.

In an embodiment therefore a coherent THz wave is efficiently generated by using an optical resonator for the idler wave and continuous and broad tunability of the frequency of the THz wave generated can desirably be achieved by altering the angle between the incident pump beam and the resonator axis.

In an embodiment of the present invention the pump radiation used for generating the THz wave is in the near infrared spectral range. It is to be noted that the non-linearly optical crystal in an embodiment is only pumped with a single pump wavelength and both a THz wave and also an idler wave are generated by the parametric process, which waves comply with the above-described law of conservation of energy and law of pulse conservation.

In that respect in an embodiment of the invention it is necessary for the THz wave generated by the parametric oscillator in the non-linearly optical crystal to be coupled out of the crystal in some way as the refractive indices of the materials typically used for the crystal are sufficiently great to cause internal total reflection in the crystal-generated THz wave. For that purpose it is desirable for one or more prism couplers, for example of silicon, to be connected to the crystal, which permit the generated THz radiation to be effectively coupled out of the crystal. In an embodiment of the invention a laser, preferably a Q-switched Nd:YAG laser, is used for pumping the non-linearly optical crystal.

In a further alternative embodiment of the invention the non-linearly optical crystal of the optically parametric oscillator is illuminated in addition to the pump radiation with a so-called seed radiation. In that case the angle orientation and the frequency of the seed beam corresponds to the idler beam generated in the crystal. It is possible in that way to achieve an increase in the THz radiation generated.

In accordance with the present invention the term THz radiation is used to denote electromagnetic radiation in the frequency range of between 10 GHz and 10 THz.

The term coherent phase-sensitive detector for detecting intensity and phase in accordance with the present invention is used to denote a photoconductive or electrooptical detector.

In that respect the term coherent in accordance with the present invention signifies that an electromagnetic pump radiation used for pumping the optically parametric oscillator and the optical reference signal used for detection at least partially have the same origin, that is to say they originate from the same source, and for that reason there is a fixed phase relationship between the difference signal of pump and idler and the THz radiation.

A photoconductive detector as is provided in an embodiment of the present invention is an optoelectronic mixer element which mixes the THz radiation to be detected with an optical reference signal which has intensity modulation at a frequency equal to the frequency of the electromagnetic THz radiation. The mixing signal derived therefrom depends both on the intensity or power of the THz radiation incident on the detector and also the phase difference between the intensity modulation of the incident optical signal and the THz signal. In an embodiment a photoconductive detector has at least one photosensitive semiconductor region between at least two read-out contacts. In dependence on the instantaneous intensity of the optical reference signal incident on the phase-sensitive detector, charge carriers are generated in the photosensitive region of the detector. The THz signal which is incident on the detector element at the same time is preferably coupled by means of a suitable receiver structure, for example an antenna, into the contacts of the detector element, which delimit the photosensitive region of the detector. The electrical alternating field which in that way is applied at the contacts leads to an ac voltage with which the detector element is acted upon. The charge carriers generated by the optical radiation move in that alternating field, in which case the current flowing through the element depends on the product of the charge carrier density generated by the optical reference signal and the applied electrical field which is produced by the THz radiation. In that way a mixing signal is directly formed in the detector from the incident THz wave and the optical reference signal.

In the case of an electrooptical detector in contrast the electromagnetic THz field incident on the detector is used to apply an electrical field to an electrooptical non-linear crystal by rectification. That changes its birefringent properties in dependence on the applied field strength of the incident THz field so that a for example linearly polarised optical reference signal which is simultaneously incident in the electrooptical crystal experiences a change in its polarisation state in dependence on the applied THz field.

The change in the polarisation state of the optical reference signal is then detected for example by means of the polarisation filter and a detector or by means of a birefringent crystal and a reference detector. The detected signal is also dependent on the mixed product of the incident THz wave and the optical reference signal.

In an embodiment of the present invention the device for generating and detecting coherent electromagnetic radiation in the THz frequency range has a source for generating an electromagnetic pump radiation at a first frequency, wherein the source for generating the electromagnetic pump radiation, the optically parametric oscillator and the coherent phase-sensitive detector are so adapted that in operation of the device at least a part of the pump radiation is passed into the optically parametric oscillator and a part of the pump radiation is passed into the coherent phase-sensitive detector. In that way the electromagnetic pump radiation for driving the optically parametric oscillator and the optical reference signal required for operation of the coherent phase-sensitive detector originate from the same source.

In that respect the general expression that the elements 'are adapted' signifies that there is provided a suitable mirror or beam guide arrangement for guiding the electromagnetic pump radiation.

In a further embodiment of the invention the optically parametric oscillator and the phase-sensitive detector are so adapted that in operation of the device at least a part of the electromagnetic pump radiation which passes through the optically parametric oscillator is passed into the phase-sensitive detector, wherein in the optically parametric oscillator electromagnetic radiation at a second frequency different from the frequency of the pump radiation and from the THz frequency is generated and wherein the optically parametric oscillator and the coherent phase-sensitive detector are so adapted that in operation of the device the electromagnetic radiation at the second frequency is incident into the coherent phase-sensitive detector in spatially heterodyned relationship with the pump radiation.

If the optically parametric oscillator is operated with a suitable electromagnetic pump radiation, then for reasons of energy and pulse conservation, besides the electromagnetic THz signal, a so-called idler signal is also generated in a third frequency range, wherein the frequency of the THz radiation is precisely the difference between frequency of the pump radiation radiated into the optically parametric oscillator and the idler signal at the third frequency. If the pump radiation passing through the non-linearly optical crystal of the optically parametric oscillator and the generated idler signal are in mutually spatially heterodyned relationship, the heterodyne signal has a beat at the frequency of the THz radiation generated in the optically parametric oscillator. By virtue of the identical formation process in the non-linearly optical crystal of the optically parametric oscillator intensity modulation of the beat signal and the electromagnetic THz radiation are coupled together in phase-locked relationship. The spatially heterodyned signal of pump and idler wave then serves as a reference signal for the coherent phase-sensitive detector.

In a further embodiment of the invention the device has a beam splitter which is arranged between the source for generating the electromagnetic pump radiation and the optically parametric oscillator and which in operation of the device divides the electromagnetic pump radiation into two parts so that the first part is passed into the optically parametric oscillator and the second part is passed into the coherent phase-sensitive detector. In that way a part of the pump radiation can be branched off for driving the coherent phase-sensitive detector before the pump radiation passes into the optically parametric oscillator.

In a further alternative embodiment of the present invention the device has a source for generating electromagnetic radiation at a second frequency, wherein the source for generating the electromagnetic radiation at the second frequency, the optically parametric oscillator and the phase-sensitive detector are so adapted that in operation of the device a first part of the electromagnetic radiation at the second frequency is passed into the optically parametric oscillator and a second part of the pump beam is passed into the phase-sensitive detector. That electromagnetic radiation at the second frequency serves as so-called seed radiation for the optically parametric oscillator and permits spectral limitation of the emitted THz radiation and an increase in the intensity of the radiated THz radiation and also permits simpler tuning of the radiated THz frequency.

In still a further embodiment of the invention the device has a beam splitter which is arranged between the source for generating the electromagnetic radiation at the second frequency and the optically parametric oscillator and which in operation of the device divides the electromagnetic radiation at the second frequency into two parts so that the first part is incident in the optically parametric oscillator and the second part is incident in the coherent phase-sensitive detector.

The device according to the invention can desirably be used in a THz spectroscopy system or in an imaging THz system.

The object is also attained by a method according to the present invention of generating and detecting coherent electromagnetic radiation in the THz frequency range, wherein an optically parametric oscillator is used for generating the electromagnetic radiation in the THz frequency range and a coherent phase-sensitive detector is used for detecting intensity and phase of the electromagnetic radiation generated by the optically parametric oscillator.

Further advantages, features and possible uses of the present invention will be apparent from the description hereinafter of preferred embodiments and the accompanying Figures.

Figure 2:
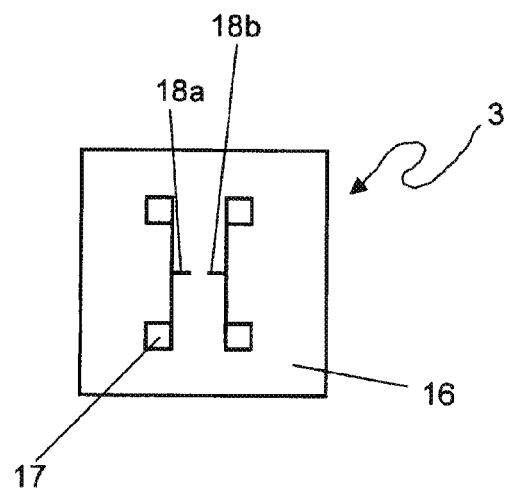
Figure 3:
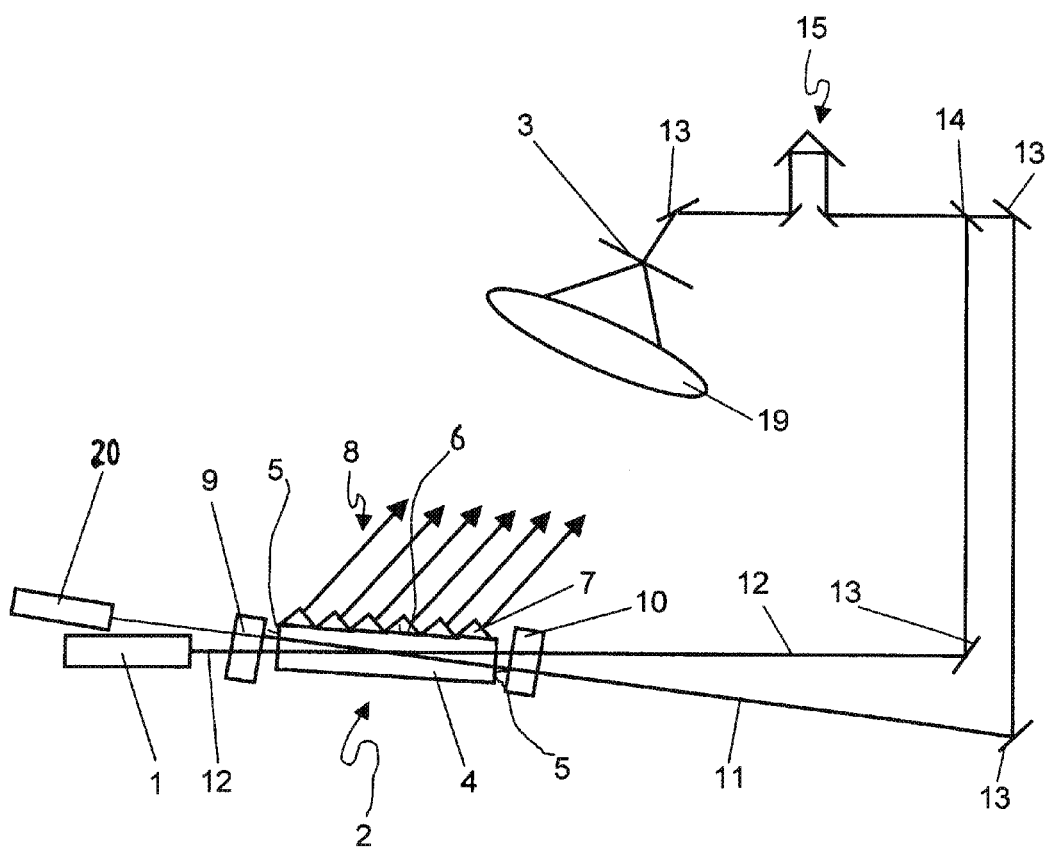
Figure 4:
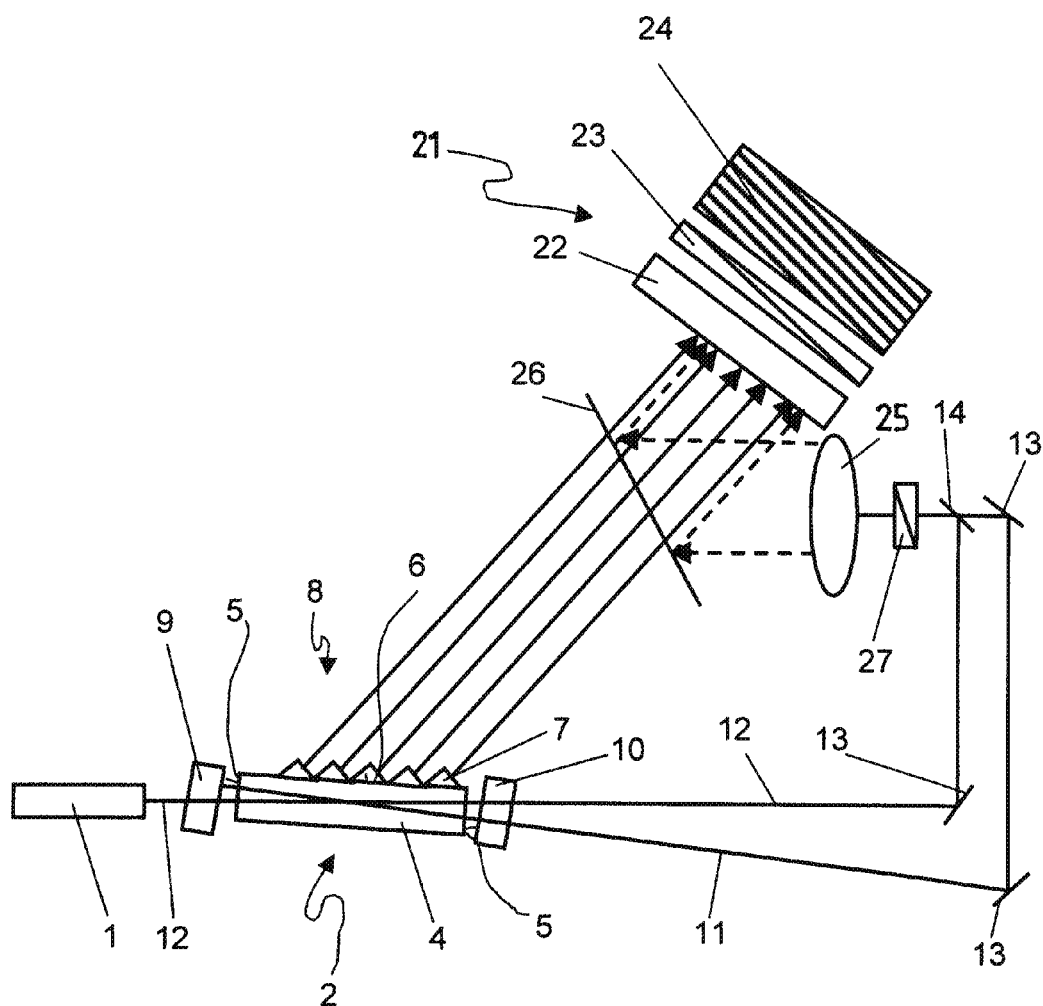

FIG. 1 diagrammatically shows a device for generating and detecting electromagnetic THz radiation in accordance with a first embodiment of the present invention, FIG. 2 diagrammatically shows the structure of a photoconductive detector in accordance with the present invention, FIG. 3 diagrammatically shows a further embodiment of the system according to the invention with a seed laser, and FIG. 4 diagrammatically shows the structure of a device according to the invention with an electrooptical detector.

FIG. 1 diagrammatically shows a first embodiment of the device according to the invention for generating and detecting coherent electromagnetic radiation in the THz frequency range. The device substantially comprises three elements, a pump laser 1, an optically parametric oscillator 2 for generating the electromagnetic radiation in the THz frequency range and a coherent phase-sensitive detector 3.

In the illustrated embodiment the pump laser 1 is a Q-switched Nd:YAG laser of a wavelength of 1.064 µm, a beam diameter of 1.5 mm, a pulse duration of 25 ns and a repetition rate of the optical pulses of 50 Hz. The typical energy per optical pulse in such a system is 30 mJ per pulse.

In the illustrated embodiment the optically parametric oscillator has a lithium niobate ($LiNdO_3$) crystal 4 of a length of 65 mm and a width and height of 5×6 mm. The coupling-in surfaces 5 of the crystal are polished to optical quality and provided with an antireflection coating for the pump wavelength. Prisms 7 of silicon are arranged on a side surface 6 of the crystal to permit better coupling-out of the THz wave 8 generated in the crystal 4. The right-angled prisms are made from highly resistive silicon. To make generation of the THz wave 8 as efficient as possible the optically parametric oscillator 2 also has two mirrors 9, 10 which form an optical resonator for the idler wave 11 generated in the crystal. In this arrangement the mirrors are of such a configuration that their substrates are only partially provided with a coating which is reflective for the idler wave 11 so that the pump radiation 12 can pass therethrough unimpededly thereby. The pump radiation 12 passing through the optically parametric oscillator 2 and the idler wave generated in the optically parametric oscillator are guided by means of an arrangement of mirrors 13 on to the photoconductive detector 3. In that case the pump wave 12 and the idler wave 11 are mutually spatially heterodyned at a beam splitter 14 so that they co-propagate downstream of the beam splitter 14 and an optical beat signal is formed at a beat frequency equal to the difference frequency between the pump wave 12 and the idler wave 11, that is to say the THz frequency. Provided upstream of the detector 3 is an optical retardation section 15 which makes it possible to alter the transit time of the reference signal formed from the pump wave 12 and the idler wave 11, that is to say to alter the phase difference between the THz wave 8 and the reference signal. In operation of the device it is to be noted that the optical path from the laser source 1 to the detector both on the THz beam path and also on the reference beam path are approximately equal in length.

In that respect in an alternative embodiment (not shown) it is desirable if the optical beam paths, unlike illustrated, are not implemented by means of bulk optics but by means of optical fibres.

The structure of the photoconductive detector 3 of FIG. 1 is shown diagrammatically on an enlarged scale in FIG. 2. The detector comprises a photoconductive semiconductor substrate, in the illustrated embodiment a gallium arsenide substrate 16 grown at low temperatures, and a metallic contact structure 17 arranged thereon. In this case the contact structure substantially comprises an interrupted dipole 18A, 18B which serves as a photoconductive switch for the reference signal comprising the spatially heterodyned pump and idler waves and as a resonant antenna for the incident THz radiation 8.

With the described arrangement, by altering the phase matching condition, that is to say by altering the angle between the pump radiation 12 and the crystal axes, it is possible to generate THz wavelengths in a range of 140 to 310 µm and detect them by means of the detector 3.

To tune the wavelength, the optically parametric oscillator 2 is arranged rotatably for that purpose so that it is possible to alter the angle of incidence of the pump radiation 12. As such tuning of the generated THz radiation also alters the beam path of the THz wave 8 radiated by the optically parametric oscillator, the detector must be correspondingly altered in its position, which makes an optical-fibre coupling of the reference signal to the detector 3 desirable.

In the embodiment shown in FIG. 1 the THz wave 8 radiated by the optically parametric oscillator is focused by means of a plastic lens 19 or also with another, for example reflecting element, on a single detector, as is diagrammatically shown in FIG. 2.

By virtue of the high level of radiated THz power however it is alternatively possible for that purpose to detect the THz wave over an area with a matrix arrangement of mutually juxtaposed detector structures which each form a respective pixel, and thus record a two-dimensional image. For that purpose it is desirable for the reference signal to be split up preferably by means of optical-fibre components into a number of signal portions of approximately equal strength, which then each serve as a reference signal for a single detector in the matrix arrangement.

FIG. 3 shows an alternative configuration of the FIG. 1 structure, this embodiment differing from the FIG. 1 embodiment in that there is additionally provided a so-called seed laser 20 which is radiated into the crystal 4 in parallel relationship with the idler signal to be expected, which is generated in the optically parametric oscillator. It is possible in that way to achieve an increase in the radiated THz power. In addition the bandwidth of the radiated THz signal 8 is limited by the additional seed laser 20.

FIG. 4 shows an alternative embodiment of the device according to the invention, wherein the photoconductive detector of FIG. 1 is replaced by an electrooptical detector 21. The illustrated electrooptical detector comprises an electrooptical ZnTe crystal 22, a polariser 23 for the optical reference signal and a CCD camera 24. The reference signal which is again generated from the spatially heterodyned pump wave 12 and the idler wave 11 is collimated and expanded by means of a lens arrangement 25 so that the beam diameter of the optical reference signal approximately corresponds to that of the THz signal 8. By means of a pellicle beam splitter 26, a thin plastic material membrane provided with a dielectric coating, expanded optical reference signals and the THz signal 8 are mutually spatially colinearly heterodyned. In that case the pellicle beam splitter 26 is transparent for the THz signal 8 while it serves as a mirror for the optical reference signal.

The optical reference signal is linearly polarised, a further polariser 27 being provided for better imposition of the polarisation state upstream of the lens arrangement 25. In the embodiments however the further polariser can also be omitted. In the electrooptical crystal 22 the linear polarisation of the reference signal is rotated in dependence on the THz field strength at the respective location in the crystal 22. The arrangement of a further polariser 23 which serves as an analyser downstream of the crystal 22 provides that that local rotation of the polarisation of the incident optical reference signal is converted in dependence on the location into a location-dependent intensity distribution which is detected over an area by means of the CCD camera.

As the instantaneous THz field strength in the crystal 22 depends both on the field amplitude and also on the phase position, it is possible with that arrangement to detect not only the intensity of the THz radiation but also the phase position thereof in relation to the optical reference signal.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

Although the foregoing description contains many details they are not to be interpreted as limitations in respect of the scope of protection of the invention, but only as examples for a preferred embodiment. Many alterations and variations are possible. Accordingly the scope of protection of the invention is not to be determined by the illustrated embodiments but by the accompanying claims and their legal equivalents.

List of References
1 pump laser
2 optically parametric oscillator
3 coherent phase-sensitive, optoelectrical detector
4 lithium niobate crystal
5 coupling-in and coupling-out surfaces of the crystal
6 side surfaces of the crystal
7 prisms
8 THz wave
9 mirror
10 mirror
11 idler wave
12 pump wave
13 mirror
14 beam splitter
15 retardation section
16 gallium arsenide substrate
17 contact structure
18A, 18B dipole
19 plastic material lens
20 seed laser
21 electrooptical detector
22 ZnTe crystal
23 polariser
24 CCD camera
25 lens arrangement
26 pellicle beam splitter
27 polariser

The invention claimed is:

1. A device for generating and detecting coherent electromagnetic radiation (8) in the THz frequency range, comprising an optically parametric oscillator (2) for generating electromagnetic radiation in the THz frequency range (8), characterised in that it has a coherent phase-sensitive detector (3, 21) for detecting intensity and phase of the electromagnetic radiation (8) generated by the optically parametric oscillator (2), wherein the optically parametric oscillator (2) and the coherent phase-sensitive detector (3, 21) are adapted that in operation of the device at least a part of electromagnetic pump radiation (12) which passes through the optically parametric oscillator (2) is passed into the coherent phase-sensitive detector (3, 21), wherein in the optically parametric oscillator (2) electromagnetic radiation is at a second frequency different from the frequency of the pump radiation (12) and from the THz frequency and wherein the optically parametric oscillator (2) and the coherent phase-sensitive detector (3, 21) are adapted that in operation of the device the electromagnetic radiation at the second frequency is incident into the coherent phase-sensitive detector (3, 21) in spatially heterodyned relationship with the pump radiation (12).

2. A device according to claim 1 characterised in that it has a source (1) for generating an electromagnetic pump radiation (12) at a first frequency, wherein the source (1) for generating the electromagnetic pump radiation (12), the optically parametric oscillator (2) and the coherent phase-sensitive detector (3, 21) are adapted that in operation of the device at least a part of the pump radiation (12) is passed into the optically parametric oscillator and a part of the pump radiation is passed into the coherent phase-sensitive detector (3, 21).

3. A device according to one of claims 1 to 2, characterised in that it has a source (20) for generating electromagnetic radiation at a second frequency, wherein the source (20) for generating the electromagnetic radiation at the second frequency, the optically parametric oscillator (2) and the coherent phase-sensitive detector (3, 21) are so adapted that in operation of the device a first part of the electromagnetic radiation at the second frequency is passed into the optically parametric oscillator (2) and a second part of the electromagnetic radiation at the second frequency is passed into the coherent phase-sensitive detector (3, 21).

4. A device according to one of claims 1 to 2, characterised in that the coherent phase-sensitive detector (21) has a matrix arrangement of pixels.

5. A device according to one of claims 1 to 2, characterised in that the coherent phase-sensitive detector is an electrooptical detector (2).

6. A device according to one of claims 1 to 2, characterised in that the coherent phase-sensitive detector is a photoconductive detector (3).

7. A THz spectroscopy system having a device according to one of claims 1 to 2.

8. An imaging THz system having a device according to one of claims 1 to 2.

9. A method of generating and detecting coherent electromagnetic radiation in the THz frequency range, wherein an optically parametric oscillator is used for generating the electromagnetic radiation in the THz frequency range, characterised in that a coherent phase-sensitive detector is used for detecting intensity and phase of the electromagnetic radiation generated by the optically parametric oscillator, wherein at least a part of electromagnetic pump radiation (12) which passes through the optically parametric oscillator (2) is passed into the coherent phase-sensitive detector (3, 21), wherein in the optically parametric oscillator (2) electromagnetic radiation is at a second frequency different from the frequency of the pump radiation (12) and from the THz frequency and wherein the electromagnetic radiation at the second frequency is incident into the coherent phase-sensitive detector (3, 21) in spatially heterodyned relationship with the pump radiation (12).

* * * * *